United States Patent [19]
Barstow et al.

[11] Patent Number: 5,203,368
[45] Date of Patent: Apr. 20, 1993

[54] MATRIX OF VALVES

[75] Inventors: Leon E. Barstow; Anthony R. Ford; Terry D. Long; Glen D. Ward, all of Tucson, Ariz.

[73] Assignee: Protein Technologies Inc., Tucson, Ariz.

[21] Appl. No.: 922,036

[22] Filed: Jul. 29, 1992

[51] Int. Cl.$^5$ ................... F16K 11/22; F16K 31/126
[52] U.S. Cl. ................... 137/240; 137/597; 137/606; 251/61.1
[58] Field of Search ........... 137/597, 606, 884, 240, 137/607; 251/61.1

[56] References Cited

U.S. PATENT DOCUMENTS

| | | |
|---|---|---|
| 3,784,169 | 1/1974 | Bockman et al. . |
| 4,008,736 | 2/1977 | Wittmann-Liebold et al. .... 137/606 |
| 4,168,724 | 9/1979 | Graffunder et al. ............. 137/606 |
| 4,281,683 | 8/1981 | Hetherington et al. . |
| 4,558,845 | 12/1985 | Hunkapiller ................ 137/606 X |
| 4,595,565 | 6/1986 | Tenhagen . |
| 4,597,412 | 7/1986 | Stark ............................ 137/606 |
| 4,668,476 | 5/1987 | Bridgham et al. . |
| 4,773,446 | 9/1988 | Farnsworth et al. ............. 137/606 |
| 4,848,387 | 7/1989 | Hon .......................... 137/606 X |
| 4,852,851 | 8/1989 | Webster ..................... 137/884 X |

OTHER PUBLICATIONS

Technical Drawing, "Assy, Valve Manifold", Protein Technologies Inc., ©1989.

Primary Examiner—Stephen M. Hepperle
Attorney, Agent, or Firm—Ogram & Teplitz

[57] ABSTRACT

A matrix of valves being formed using a sandwich of three layers with a pliable membrane interposed between two of the layers. Supply channels and delivery channels are created through etching, routing, or other such means on the middle layer. Each supply channel communicates with all of the delivery channels via a valve location which is opened or closed by pneumatic pressure on the pliable membrane. Movement of the pliable membrane is affected through suction or pressure as communicated via holes in the overlying layer. In this manner, selected supply and delivery lines are connected by appropriate suction being placed on the membrane. Selected valves are simultaneously opened to provide parallel operations.

29 Claims, 7 Drawing Sheets

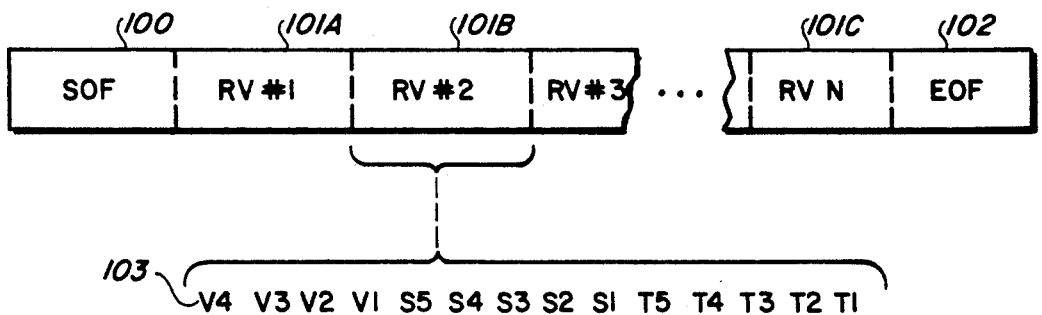
—Fig. 10—
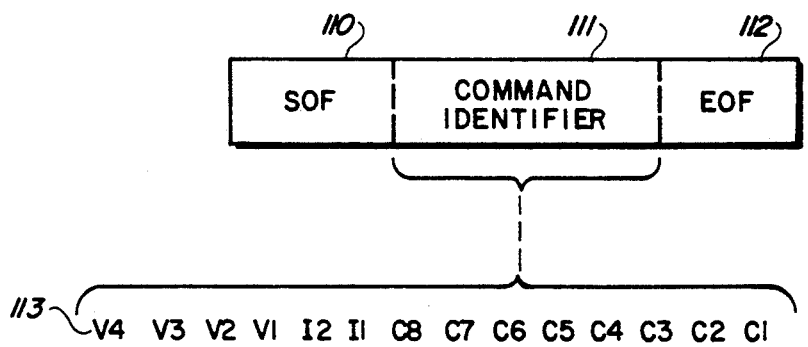
—Fig. 11—

MATRIX OF VALVES

BACKGROUND OF THE INVENTION

This invention relates generally to valves used to control flow of liquid or gaseous materials and specifically to valves used in peptide synthesis.

Within this discussion, the use of the invention in relation to solid phase peptide synthesis will be used as an example. Those of ordinary skill in the art readily recognize various other applications where such valving proves commercially advantageous including, but not limited to, DNA synthesis and protein sequencing.

The solid phase method of peptide synthesis was first introduced by Professor R. B. Merrifield in 1964. This method drastically reduced the time required to chemically synthesize peptides by substantially simplifying the isolation and purification steps required in a chemical synthesis. This simplification was accomplished by attaching the carboxyl end of the C-terminal amino acid to an insoluble resin support (usually cross-linked polystyrene). All the chemical isolation and purification steps were then conducted on this insolubilized system. The method has been applied to the synthesis of a very large number of peptides on both a laboratory and commercial scale.

Professor Merrifield received a Nobel Prize in Chemistry for his contributions to science in 1985. Hundreds of scientific papers have been published describing variations on Merrifield's basic chemical approach. Several instruments have been designed and built by both academic and commercial laboratories to automate the solid phase method. The method has also been applied to the synthesis of deoxyribonucleic (DNA), ribonucleic (RNA), and polysaccharides.

In a typical solid phase synthesis of a peptide, there is a covalent attachment between the carboxyl end of an alpha protected amino acid and an insoluble resin support that is typically 1 to 2 percent divinylbenzene cross linked polystyrene with bead size of 200–400 mesh.

The next amino acid in the peptide chain is added by a series of chemical reactions that start with deprotection of the alpha amino group, washes for purification, and the coupling of a new protected amino acid followed by further washing for purification.

This process is repeated for each amino acid in the peptide chain. Chemical reactions and washing steps can be automated and a number of commercial instruments are now available for carrying out this task.

Once the peptide chain is constructed, it must be removed from the polymer support, the side chain protecting groups removed, isolated and purified.

For a good review of the state of art in peptide synthesis, see U.S. Pat. No. 4,668,476, entitled "Automated Peptide Synthesis Apparatus" issued to Bridgham et al. on May 26, 1987, incorporated hereinto by reference.

Automated production of peptide synthesis has taken two basic approaches: (i) the use of robotic arms to move and physically deposit the selected amino acid or reagent into the reaction vessel; or (ii) selectively channeling a flow of amino acid or reagent into the reaction vessel.

Robotic arms have provided a great deal of automation to be process. An articulated arm, once programmed to create the particular peptide, selects the appropriate vial of material and deposits that material into the reaction vessel. Through a sequence of deposits and waits, the desired peptide is produced.

Although the robotic method offers some distinct advantages, the mechanical movement of the amino acids is susceptible to spills. Another disadvantage is the time required to physically move the container and then replace it. Yet another disadvantage is the fact that robotic mechanisms are almost by definition single process type; that is, only one synthesis is possible at any one time.

Other disadvantages of the robotic system is that it is an "open system" which creates hazards to workers and is susceptible to contamination from the air. Still further, the robotic systems are limited in volume and are sequential in nature (one process at a time).

Because of these constraints on the robotics approach, most applications do not use the articulated arm for the synthesis of peptides.

The vast majority of applications utilize a valving operation to deliver the amino acid and reagent materials to the reaction chamber. In these devices, a supply of selected amino acids and reagent material are positioned to supply, via valves, the reaction vessel. In this manner, through selective activation or individual valves, the amino acid or reagent is communicated to the reaction vessel to build the peptide.

The use of valves eliminates the need to physically move containers and as such operates much faster and without the possibility of spills encountered with the robotic approach.

To this end, a larger number of patents have been obtained which relate to the valves themselves and their control. Examples of these patents include: U.S. Pat. No. 4,597,412, entitled "Valve for Sequential Chemical Operations" issued to Stark on Jul. 1, 1986; U.S. Pat. No. 4,595,565, entitled "Equipment for Mixing Liquid Reactants" issued to Tenhagen on Jun. 17, 1986; U.S. Pat. No. 4,281,683, entitled "Modular Multiple-Fluid Component Selection and Delivery System" issued to Hetherington et al. on Aug. 4, 1981; U.S. Pat. No. 3,784,169, entitled "Method of and Apparatus for the Controlled Mixing of Two Reactive Components" issued to Bockmann et al. on Jan. 8, 1974; and, U.S. Pat. No. 4,848,387, entitled "Method and Apparatus for Segregated Introduction of Two Liquids into a Chemical Reactor Vessel at a Common Entry Point" issued to Hon on Jul. 18, 1989, U.S. Pat. No. 4,008,736, entitled "Valve Arrangement for Distributing Fluids" issued to Wittman-Liebold et al. on Feb. 22, 1977.

Additionally, many different companies have tried their own unique designs for creating a grouping of valves. One such example is the valve used by Protein Technologies Inc. for its PS3 Peptide Synthesizer.

In all of these cases, the valve arrangements are of such complexity that only a single group of valves is possible, all of which address a single reaction vessel. This restriction is forced upon them by their own complex piping requirements.

Furthermore, these devices have some intrinsic drawbacks both in operating time and quality control. Once a particular liquid has passed through a valve and into the conduit to the reaction vessel, a residue is left behind. If not cleaned thoroughly, this residue from the previous liquid will affect later liquids and thus have a negative effect upon the quality of the peptide produced. Because of this concern, the physical structure of the valve and "pipes", conduits, or channels connecting everything is of pronounce importance. If improperly done, dead volumes are created which shield the residue from cleaning.

As the industry has expanded, the need for faster, more accurate, and of higher quality synthesis has increased. These above devices have not met this demand.

SUMMARY OF THE INVENTION

The invention is a peptide synthesizer involving a matrix of valves being formed using a sandwich of three layers with a pliable membrane interposed between each of the layers. Supply channels and delivery channels are created through etching, routing, or other such means on the middle layer. Each supply channel communicates with all of the delivery channels via a valve location which is opened or closed by the pliable membrane. Movement of the pliable membrane is effected through suction or pressure as communicated via holes in the overlying layer. In this manner, selected supply and delivery channels are connected simply by applying an appropriate suction on the membrane.

In accordance with the preferred embodiment of the invention, an apparatus is provided for automatically constructing peptides simultaneously. The apparatus contains a free standing computer that is used for entering the amino acid sequence in each peptide chain and the chemistry(s) used to construct that sequence. Ideally, the apparatus has supply bottles for 20 different alpha amino protected amino acids, two solvents and four reagents. Preferably, the vesels for the alpha amino protected amino acids are at the front of the apparatus for ease in filling. The solvents and reagents are contained in a cabinet directly below the amino acid and reaction system. In the preferred embodiment, twelve reaction vessels are positioned across the front top of the instrument. These reaction vessels are held in place by a specially constructed spring loaded ball and socket system.

It is essential that the protocol for each peptide synthesis be carried out precisely. The apparatus, therefore, contains a fluid sensor system that monitors each reaction vessel to ensure the integrity of the synthesis. Any fluid error detected by the system, results in the shut down of that particular synthesis until there is operator intervention to correct the problem.

Both the rate and completion of chemical reactions in peptide synthesis are dependent upon the structure of the protected amino acid to be coupled and the structure of the growing peptide chain. There are 20 natural occurring amino acids that are used the vast majority of time in peptide synthesis. This limits the number of variables for that portion of the synthesis. There are, however, a virtually infinite number of possibilities for the structure of growing peptide chain. Under normal conditions, the two chemical reactions (coupling and deprotection) proceed under standard conditions. However, there are some chemical reactions that are slower and less effective. This automated apparatus compensates for those by allowing for more vigorous conditions, (i.e., longer reaction times, multiple identical reactions, or increased reagent concentration to push these reactions toward completion).

This apparatus, which basically functions as twelve independent peptide synthesizers, is simplified by the use of a unique matrix valve block described below. This matrix valve block eliminates the vast majority of the complex plumbing that would otherwise be required for building an apparatus of this type.

This matrix valve block allows the independent filling of a multiple of receiving vessels from a multiple of supply reservoirs in a truly simultaneous fashion. The valve block also eliminates a plethora of tubing and connectors due to the fluid conduits machine in the valve block itself and the surface mounted solenoid pilot valves.

The valve block is truly a matrix of valves. As example, if there are to be N supply lines feeding M reaction vessels, the valve block is $N \times M$; thereby permitting any of the N supply channels to feed into any of the M reaction vessels.

Through computer control, supply Si is released to reaction vessel Rj for a selected amount of time to provide the proper reaction; while, simultaneously, another supply Sk is being released to reaction vessel R1.

The truly independent nature of the system allows the scale (amount of peptide to be made for a particular reaction) to be varied from reaction vessel to reaction vessel. This feature reduces the amount of reagent required by not forcing the operator to produce more material than may be necessary for the subsequent biological experiments.

The matrix valve block is totally enclosed and therefore does not allow hazardous solvent vapors to escape into the atmosphere as is the case with commercial robotic systems. All reactions are done in inert nitrogen or aron atmosphere.

Since this apparatus is truly simultaneous, it is significantly faster than robotic systems where each synthesis is actually done individually and sequentially.

After all amino acids have been assembled on the polymer support, the peptide synthesis is complete. Under computer control, this apparatus removes the peptide from the solid phase support and any side chain protecting groups. The cleaved and full deprotected peptide is ot in solution and is automatically transferred from a reaction vessel to a separate collection tube. The tube is removed from the apparatus and the peptide is isolated from solution and purified.

Brief Description of Drawings

FIG. 10 is a graphical representation of the preferred data string used by the computer to control the peptide synthesis operation.

FIG. 11 is a graphical representation of the preferred command string used by the computer to direct operation of, and solicit status information from, the peptide synthesizer.

DRAWINGS IN DETAIL

The solid phase method along with its automation has made peptides readily available to researchers. However, the need for small quantities (1 to 100 milligrams) for manh research groups is far greater than can be produced on currently available equipment that basically does one synthesis at a time.

Earlier machines have increased their thoughput by using sequential syntheses to eliminate machine downtime during off working hours or by using robotic systems that manipulate a large number of syntheses in a sequential fashion. These systems are all very slow and offer minimal flexibility in scale, chemistry and reaction conditions.

As the pace of research in biotechnology increases, the number of synthetic peptides needed has increased substantially. The current automated synthesizers are not able to keep pace with the demand.

Figure 1:
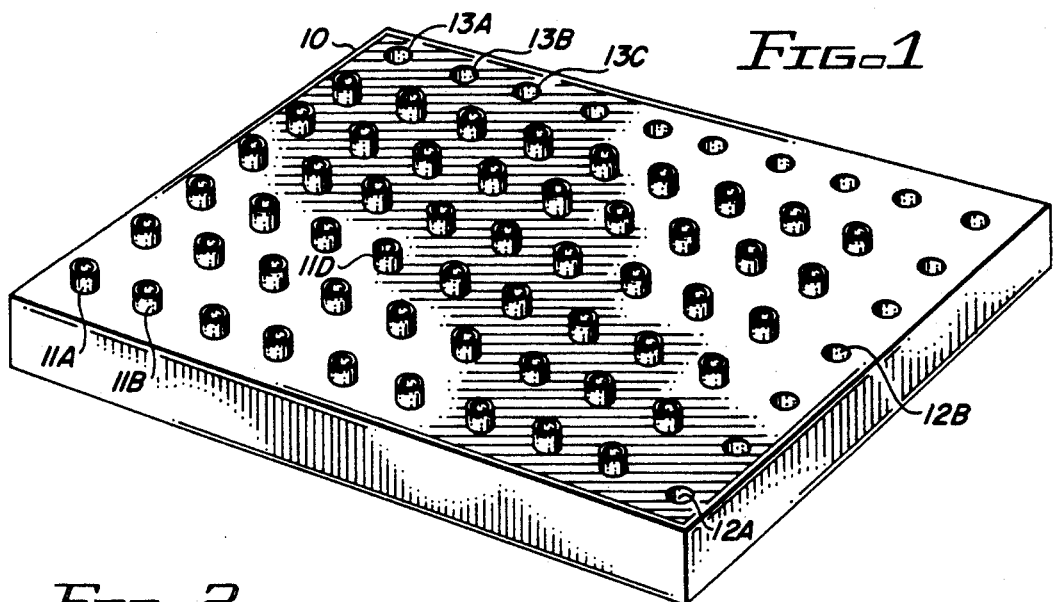
FIG. 1 is a perspective view of an embodiment of the valve block of the present invention.

FIG. 1 is a perspective view of an embodiment of the valve block of the present invention.

Valve block 10 is a generally flat arrangement having a plurality of suction connectors such as 11A, 11B, and 11D, arranged in a matrix relationship. In this embodiment, valve block 10 is composed of a 6×9 grouping of valves. That is, valve block 10 is able to have six different liquids selectively communicated to nine different reaction vessels.

Supply holes 13A, 13b, 13C, etc. accept piping which communicates with the reaction vessels. Those of ordinary skill in the art readily recognize various mechanisms which are capable of providing an interlocking arrangement between the holes, such as 13A, and the piping (not shown) going to the reaction vessel.

Supply holes, such as 12A and 12B, also accept piping from the supply reservoirs of amino acids, coupling agents, and deprotection materials.

In this application, assume an amino acid, X, is supplied to supply hole 12A and amino acid Y is supplied to 12B. Through activation of suction via 11A, amino acid X is communicated to the reaction vessel associated with 13A. In like fashion, suction provided at 11B permits amino acid X to be communicated to the reaction vessel associated with 13B; and suction to 11D, permits amino acid Y to be communicated to the reaction vessel associated with 13C.

Note the important aspect of the present invention, all three valves, 11A, 11B, and 11D are simultaneously open; supplies of amino acids or other desired material are capable of being delivered through the use of the matrix of valves at the same exact time.

In the present embodiment, it is possible to have nine different valves opened so that each of the nine reaction vessels is receiving materials simultaneously.

Figure 2:
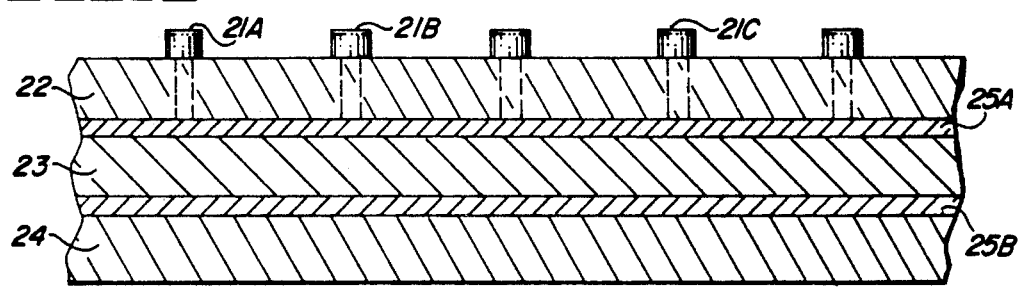
FIG. 2 is a cross sectional view of the valve block first described in FIG. 1 illustrating the sandwich approach.

FIG. 2 is a cross sectional view of the valve block first described in FIG. 1 illustrating the sandwich approach.

The valve block is composed of a sandwich of several layers. Bottom layer 24 is a substantially flat piece of material which has overlaying it protective layer 25B. Protective layer 25B is used in this embodiment to protect layer 24 from reacting with the amino acids and other such caustic material which may be communicated via the valves and channels.

Layer 23 is composed of a material which is resistant to reaction to the amino acids and such. In the preferred embodiment, layer 23 is composed of polyphenylene sulfide. In layer 23, channels and holes are created to carry the liquids from the supply reservoirs to the reaction vessels.

Protective layer 25A protects layer 22 from the amino acids. Layer 22 is used to create the valving locations which communicate with the pump (not shown) via suction conneters such as 21A, 21B, and 21C.

By securing this sandwich through the use of screws or other such fasteners, the assembly becomes a rigid body suitable for a variety of applications.

Figure 3:
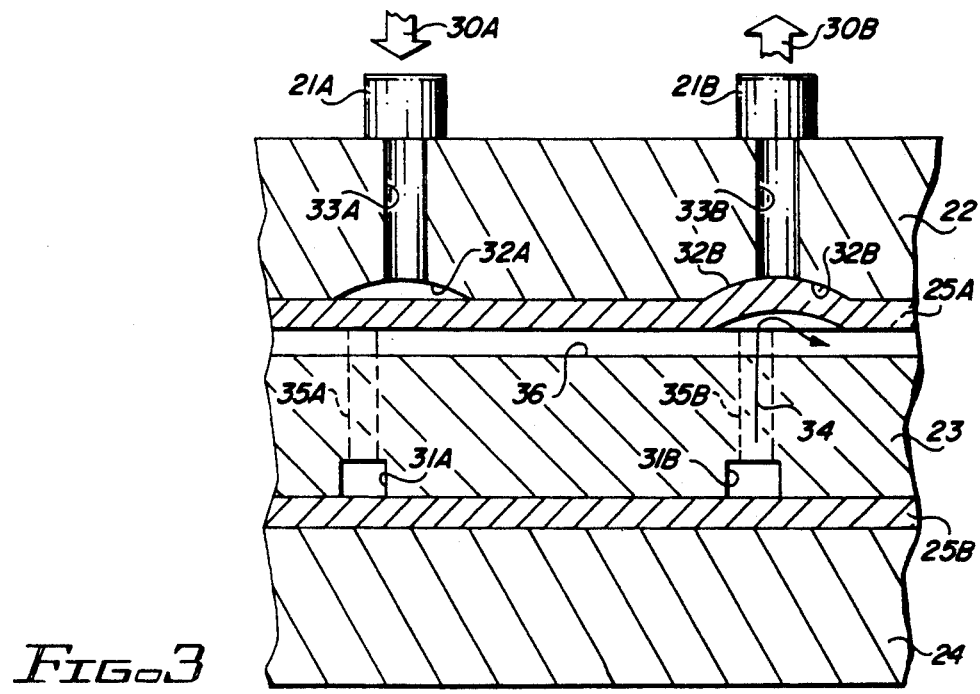
FIG. 3 is a close-up cross sectional view of the valve block of FIG. 1 illustrating an open and a closed valve arrangement.

FIG. 3 is a close-up cross sectional view of the valve block of FIG. 1 illustrating an open and a closed valve arrangement.

As noted earlier, the valve block is constructed of a sandwich of layer 22, protective layer 25A, layer 23, protective layer 25B, and layer 24. Within layer 23 are created channels for the communication of the liquids and gasses. Channels 31A and 31B extend perpendicular to the plane of the drawing and are used to supply the amino acids and other materials from the reservoirs. These channels are created through either a grinding action, routing, etching, or a similar manner known to those in the art.

Channels 31A and 31B communicate with the valves via holes 35A and 35B respectively. Valving location 32A and 32B are structured to overlay their associated supply hole (35A and 35B respectively) and the delivery channel 36.

In this embodiment, delivery channel 36 is created on the opposite side of layer 23 and substantially perpendicular to supply channels 31A and 31B. This arrangement permits easy access between supply and delivery channels via the valves and provides a matrix of valves.

A closed valve is illustrated at valving location 32A. Pressure 30A is provided via suction connector 21A and hole 33A which presses protective layer 25A firmly against layer 23 over supply hole 35A. Liquids or gasses from supply channel 31A are not able to pass; hence valve location 32A is closed.

Valving location 32B is open. Suction 30B is provided by a pump, not shown, via suction connector 21B and hole 33B. This pulls a portion of protective layer 25A up into the cavity of valving location 32B; thereby permitting liquids or gases from supply channel 31B to flow up through supply hole 35B and into channel 36 as illustrated by arrow 34.

In the preferred embodiment, valves are normally closed (pneumatic pressure supplied to them). If a valve is to be opened, then the pressure is released to that valve and a suction is provided to the valve.

Although in the preferred embodiment's application of peptide synthesis, only one valve per delivery channel is open, there are some situations where multiple valves are simultaneously opened per channel to expedite the operation.

Note that a single supply channel is able to provide liquids or gasses to any selected group of delivery channels.

Figure 4:
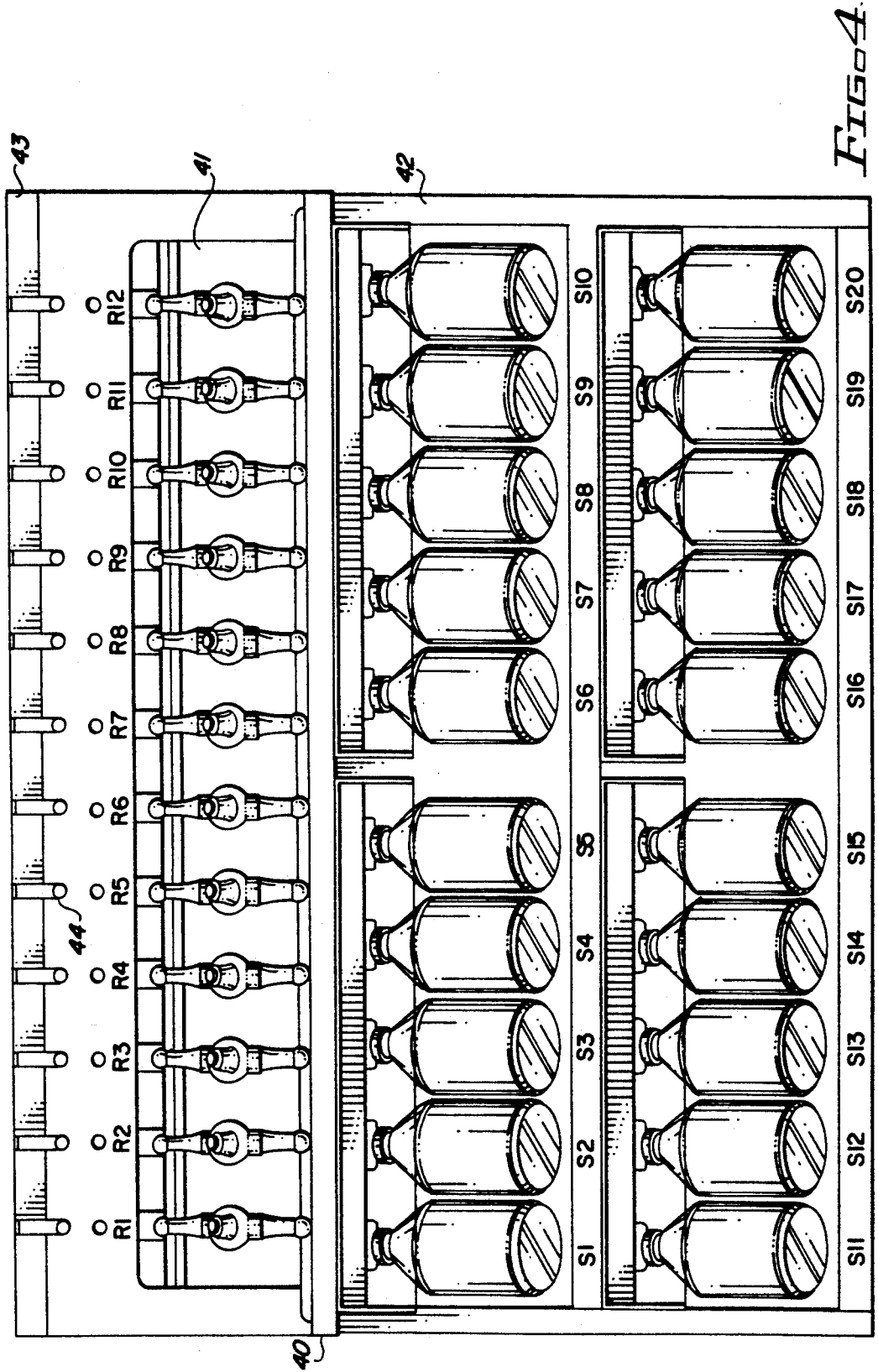
FIG. 4 is a frontal view of the preferred embodiment of the invention illustrating the supply bottles and reaction vessels.

FIG. 4 is a frontal view of the preferred embodiment of the invention illustrating the supply bottles and reaction vessels.

In this embodiment, both the reaction vessels and the supply reservoirs are accessible at the front of the apparatus. As shown, this embodiment utilizes twelve different reaction vessels 41, R1-R12. Each reacton vessel is removable via operation of associated release mechanisms 43. As example, reaction vessel R5 is removable through operation of release mechanism 44.

Amino acids are kept in supply reservoirs 42, S1-S20. Although the device is equipped with sensors to determine when a supply reservoir is empty (as discussed later), the supply reservoirs are constructed of a clear material such as glass to permit a quick visual check on their status.

Using the valve block discussed earlier permits any one of the twenty liquids from the supply reservoirs to be selectively communicated to any one of the twelve reacton vessels.

Figure 5:
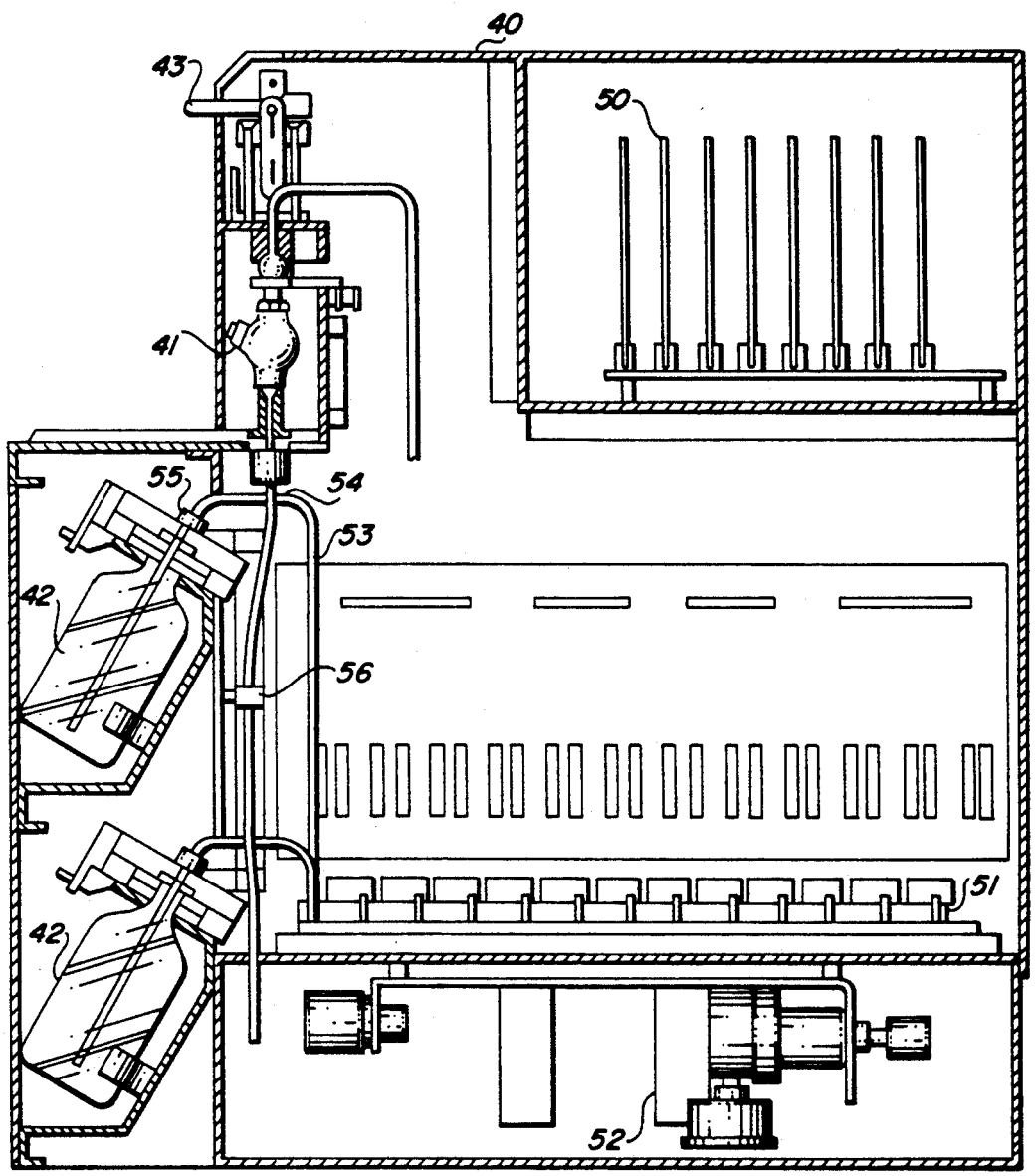
FIG. 5 is a side view of the preferred embodiment in block form, illustrating the arrangements of the various components of the preferred peptide synthesizer.

FIG. 5 is a side view of the preferred embodiment in block form illustrating the arrangements of the various components of the preferred peptide synthesizer.

As discussed before, supply reservoirs 42, reaction vessels 41, and release mechanisms 43 are all positioned at the front of the machine to provide quick access for removal and replacement.

Sensor 55 is used to determine if there is liquid passing from the supply reservoir. The liquid is communicated via a pneumatic action and piping 53 to valve block 51. Pneumatic inlet valves 52 are used to provide this pumping action and is also used to provide the suction and pressure necessary for operation of the valves, as discussed before, within valve block 51.

The liquids are communicated to the reaction vessel via tubing 54 from the valve block 51.

Operation of the entire machine is controlled by computer 50. In this manner, computer 50 is able to monitor the status of the supply reservoirs 42 via sensors, such as sensor 55. The liquid volumes being transfered is monitored by sensor 56 which communicates with valve block 51.

In operation, tube 54 is empty untils such time as a liquid is to be communicated, upon opening of the appropriate valve on valve block 51, liquid is communicated into tube 54. The length of tube 54 between sensor 56 and valve block 57 is fixed in length and volume; hence, when sensor 56 senses the presence of fluid, this establishes a known reference volume to be used by controller 50. Additionally volumes are established by timing the opening of the valve in valve block 57.

As an automated system, in this embodiment, twelve different reactions are simultaneously performed without operator intervention nor the physical movement of the supply reservoirs.

Figure 6:
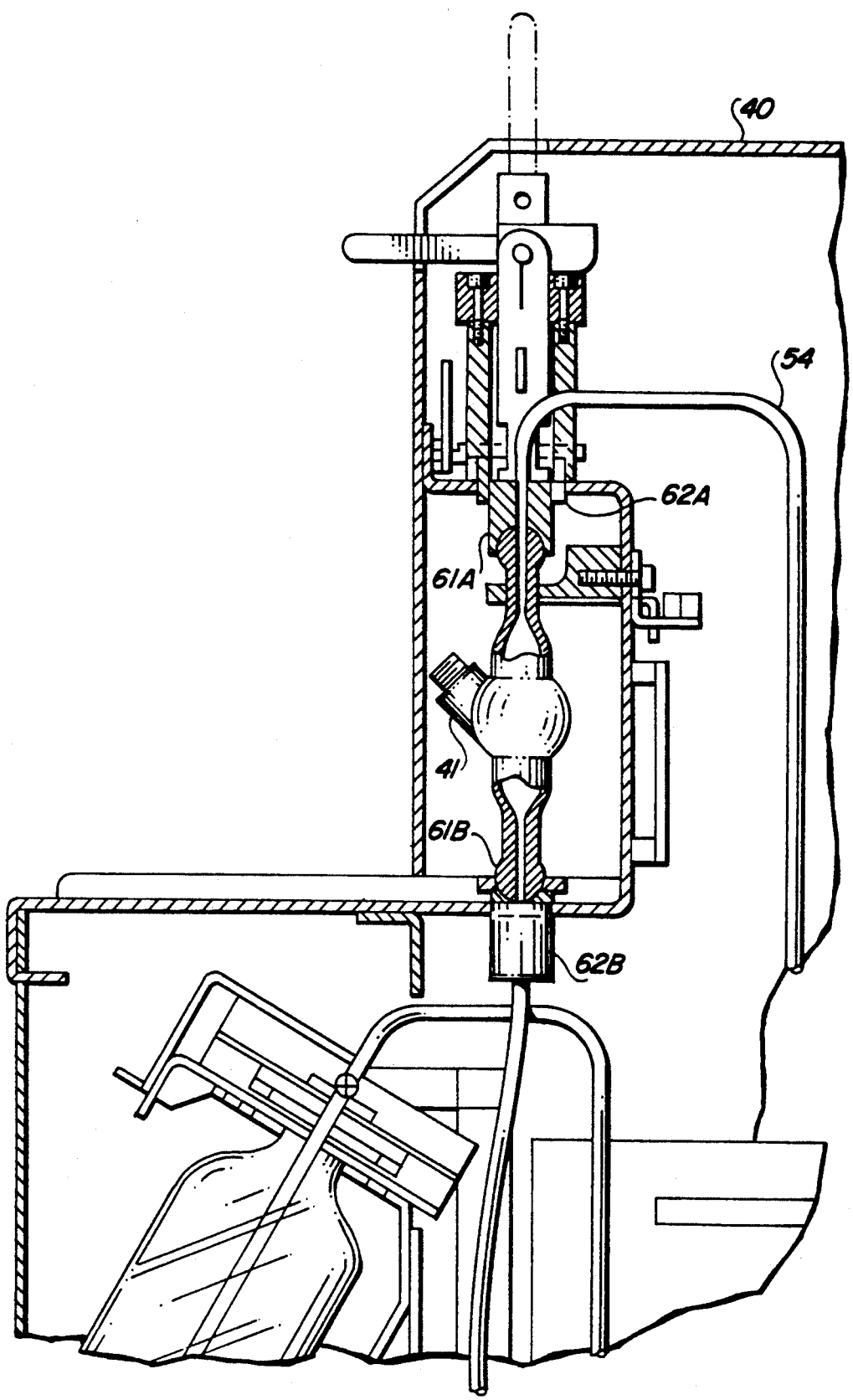
FIG. 6 is a close up side view of the reaction vessel used in the embodiment of FIG. 5.

FIG. 6 is a close up side view of the reaction vessel used in the embodiment of FIG. 5.

The ability to easily remove the reaction vessels from the device is an important aspect in that it reduces down time of the machine between the peptide synthesis and also reduces the chances of spillage.

Reaction vessel 41 has at its upper end ball seat 61A which automatically closes when pressure is released via release mechanism 43 pressing down onto ball seat 61A via connector 62A. Tubing 54 extends through connector 62A to properly communicate with reaction vessel 41.

Similarly, at the bottom end of reaction vessel 41 is ball seat 61B which communicates via connector 62B with a gas stream to provide proper agitation within the reaction vessel.

In this manner, release of the reaction vessel 41 by release 43 permits the reaction vessel to be quickly and easily removed from the device. Once so removed, another reaction vessel is readily inserted and the removed vessel placed in storage or communicated to the user needing the therein contained peptide.

Figure 7:
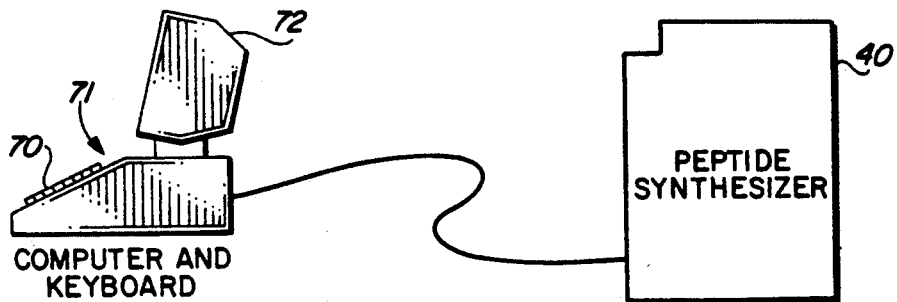
FIG. 7 is a block diagram illustrating the computer/operator interface connected with the preferred peptide synthesizer.

FIG. 7 is a block diagram illustrating the computer-/operator interface connected with the preferred peptide synthesizer.

In the preferred embodiment, an external computer system 71 including a keyboard 70 and video screen 72, links with and directs the peptide synthesizer 40 discussed before. In this embodiment, the software operation consists of two pieces of software that work together.

At the external computer system 71 level, a multitasking kernel is constantly running, receiving messages from the peptide synthesizer 40, handling user interface tasks, and sending commands to the peptide synthesizer 40.

This multitasking kernel consists of a Common User Access standard (as developed by International Business Machines "CUA" interface that allows the user to start/stop up to twelve operations at once on the peptide synthesizer, while at the same time, the user is able to perform various editing operation on the external computer. These editing functions are useful in defining the peptide required to be synthesized.

The multitasking kernel is event driven, and the whole process is linked to the peptide synthesizer 40 through message protocols.

The second piece of software resides in the peptide synthesizer and is installed on a motherboard arrangement. This software uses a variety of interrupts to monitor its tasks, events, and communications with the external computer. Its entire operation is interrupt driven and the peptide synthesizer acts as a "slave" device to the external computer 71.

The external computer 71 initiates all communication which causes an interrupt at the peptide synthesizer 40 level.

Figure 8:
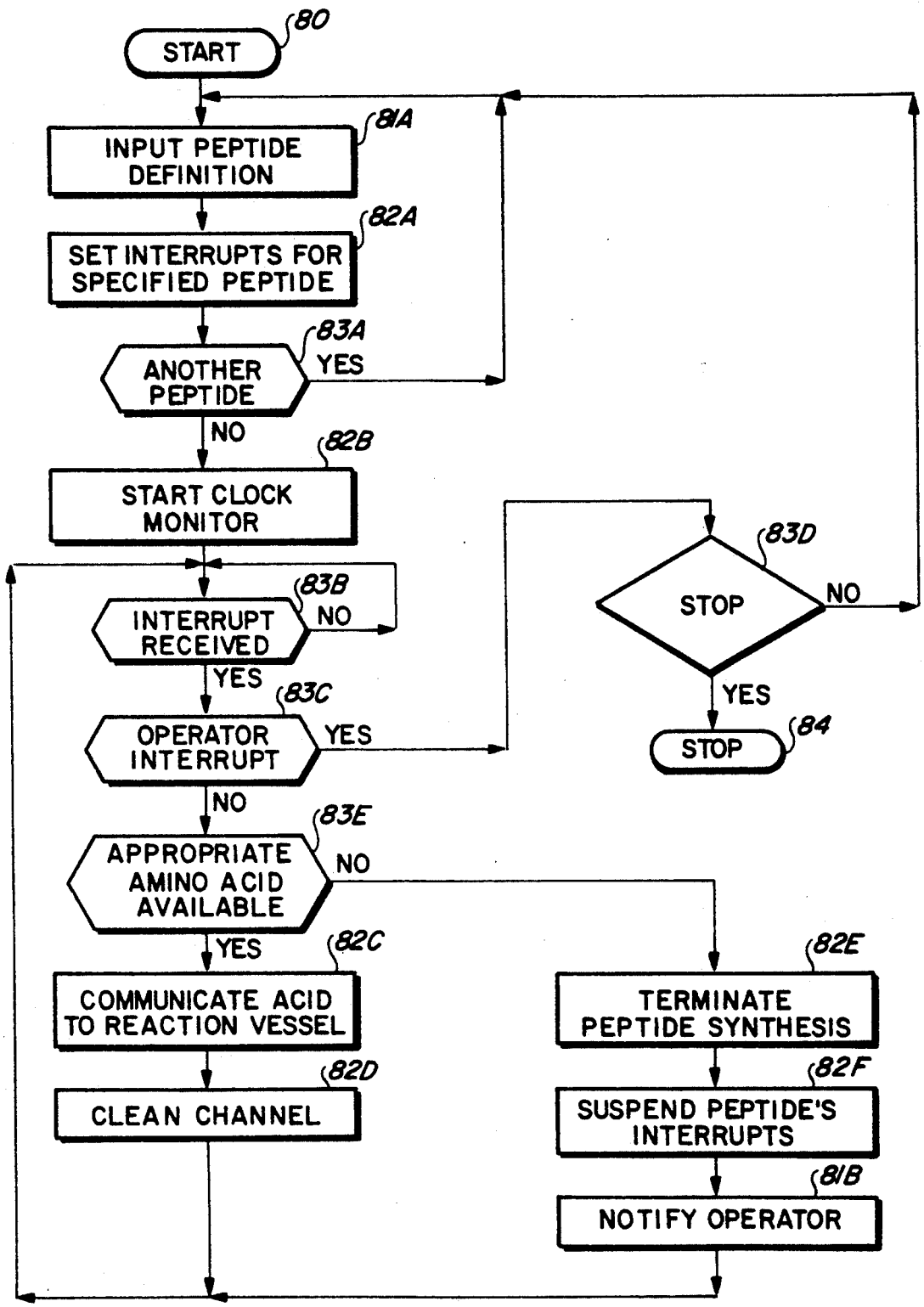
FIG. 8 is a flow-chart of the preferred operation of the computer used in controlling the peptide synthesizer.

FIG. 8 is a flow-chart of the preferred operation of the computer used in controlling the peptide synthesizer 40.

Once the program has been started, 80, the operator establishes the peptide definition 81A. This definition takes a variety of forms including: a library definition such as, "Produce Peptide I.D. No. 367"; a chemical definition of the peptide; or, a step-wise definition of what must be done.

Based upon the peptide definition, the external computer establishes a set of interrupts and commands 82A which accomplish the desire of the operator.

If another peptide is also desired, 83A, then the program loops back to permit another peptide definition, 81A; if not, the clock monitor is begun 82B.

Utilizing the established interrupts, the program monitors to see if an interrupt has been received 83B. An interrupt may be internally generated or be derived from the program's own established interrupts which were created for a particular peptide synthesis.

The interrupt is analyzed to see if it is an operator interrupt 83C. If it is, the operator chooses, 83D, to either stop 84, or define another peptide 81A. A stop operation 84 is typically done in an emergency situation since the work being performed in the reaction vessels may be lost if not closely monitored.

The ability for an operator to choose to define another peptide even after the program has been initiated is important; in this situation, the operator is given a wide degree of freedom since now the peptide synthesizer may be started with some set of peptides, say even different ones, and then later, as the need arises, more peptides are added. The peptide synthesizer is not "tied up" once it has begun but rather is a dynamic operation in which the various peptide syntheses going on may be at very different levels of completion.

In this manner, the entire system acts as twelve independent synthesizers permitting the user to start and stop any one reaction at will without disturbing the other reactions.

If the interrupt is not generated by the operator, the interrupt wa created by the program at 82A and now the appropriate amino acid or other operation must be performed at the current time. Using the information associated with the interrupt, a check is made to see if the needed amino acid (or other such liquid) is available 83E.

If the liquid is not available, then that particular peptide synthesis is terminated 82E; that peptide's interrupts are suspended 82F, and the operator is notified 81B that the necessary reservoir is empty. The program continues monitoring for interrupts 83B.

Note that in this situation, the process continues for all of the other peptide syntheses in process; only the synthesis which requires amino acid from the "empty" reservoir is suspended. The operator is able to replenish the reservoir and initiate the suspended synthesis again.

If we assume that the appropriate amino acid is available 83E, then the external computer directs the peptide synthesizer to communicate the proper amount to the reaction vessel. Once the amino acid is communicated, the channel to the reaction vessel is cleared of all fluid for subsequent operations. Those of ordinary skill in the art readily recognize various methods to clear or clean the channel. In the preferred embodiment, nitrogen is directed into the channel to clear it followed by solvent to clean it.

Once cleaned, the program returns to await another interrupt 83B.

In this manner, the program provides a dynamic framework upon which multiple peptides can simultaneously and independently be generated.

Figure 9:
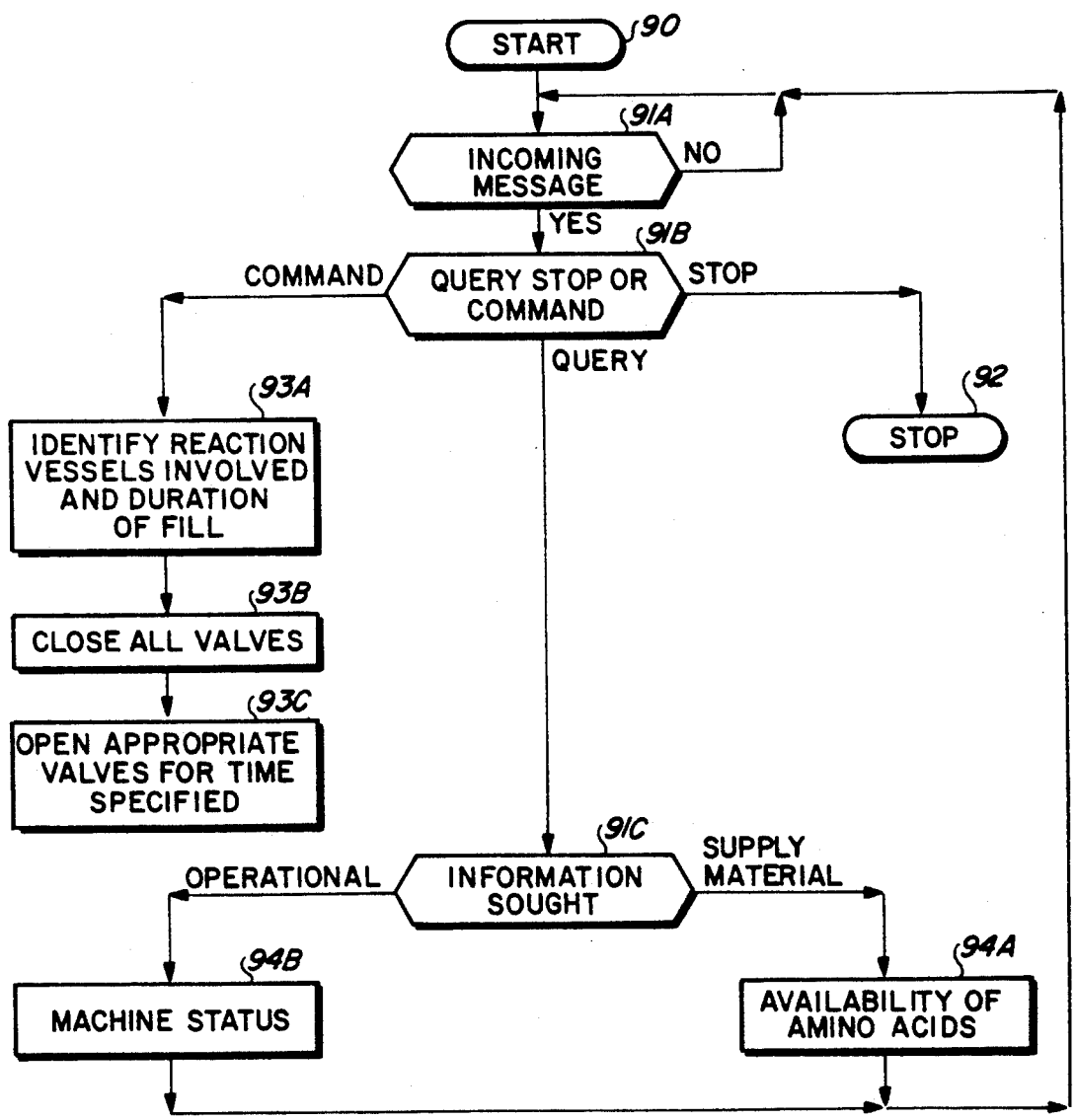
FIG. 9 is a flow-chart of the preferred operation of the peptide synthesizer.

FIG. 9 is a flow-chart of the preferred operation of the peptide synthesizer.

Once start 90 has occurred, the program check for incoming messages 91A and loops back if one has not been received. The peptide synthesizer is a slave device to the external computer and as such it checks for incoming messages to determine what needs to be done.

Once a messge has been received, a determination is made as to the nature of the command 91B. Commands generally fall into three different categories: Query, Stop, and Command.

If the message is a query, then a determination is made as to the nature of the information sought 91C. Operational type queries require that the machine status 94B, be communicated to the external computer; then the program returns to await another incoming message 91A. If the query seeks information as to the supplies within the peptide synthesizer, the availability of the amino acids (and other liquids) is communicated back to the external computer 94A and the program returns to await another incoming message 91A.

If the incoming message was determined, 91B, to be a step, then the operation of the program, and hence the synthesizer, is stopped 92.

If the incoming message was determined, 91B, to be a command, then the command is broken down to determine which reaction vessels are involved and the time required for the amino acid to be communicated 93A. All valves within the valve block are closed 93B; and, the appropriate valves are opened for the time specified in the command 93C. Once the proper amount of amino acid has been communicated to the reaction vessel, the program returns to monitor for incoming messages 91A.

In this manner, the program structures the peptide synthesizer to react only to the commands of the external computer. FIG. 10 is a graphical representation of the preferred data string used by the computer to control the peptide synthesis operation.

Data communicated from the external computer to the peptide synthesizer is structured as a sting having a Start-Of-File 100 followed by N fourteen bit words such as 101A, 101B, and 101C. The transmission is terminated by an End-Of-File 102.

Each of the fourteen bit words 103 is decoded into a reaction vessel identification number 104A (four bits), a supply material number (five bits) 104B, and a time value (five bits) 104C.

The reaction vessel number provides a successive value going from 1 to N, the number of reaction vessels for the particular peptide synthesizer. Hence, the reaction vessel for segment 101A would be designated 0001; for 101B the reaction vessel number is 0010; etc..

If no action is to be taken with a particular reaction vessel, the supply material segment reads 00000. Otherwise, the supply material number indicates the source of the material (i.e. amino acid for reservoir seven-"00111") which is to be communicated to the specific reaction vessel.

The time of the valve opening is given in tenths of seconds. This condition varies according the channel dimensions within the valve block and the pressure used to communicate the liquid. Time is used to establish how much liquid is communicated.

FIG. 11 is a graphical representation of the preferred command string used by the computer to direct operation of, and solicit status information from, the peptide synthesizer.

Information requests are communicated via a string having a Start-Of-File 110 followed by a fourteen bit command 111 and then an End-Of-File 112. The fourteen bit command string 113 is composed of a four bit identifier which is 0000. This structure is used to distinguish this type of communication from that illustrated in FIG. 10.

The two bit Identifier 114B's value is used to indicate if a machine status, supply status, operational command, or an emergency shutdown is being communicated.

Command Identifier 114C is an eight bit command which specifies which command is to be carried out. The range of commands varies dramatically from one embodiment to another and the commands are adjusted accordingly.

It is clear from the foregoing that the present invention creates a highly improved peptide synthesizer with the capability to simultaneously synthesize peptides.

What is claimed is:

1. A valving system comprising:
   a) a pneumatic means for providing a suction force and a pressure force;

b) a valve block having,
　1) a first layer having a substantially flat first surface,
　2) a second layer having at least two supply channels and at least two delivery channels, said second layer also having at least four valving locations for communicating flowing material from each of said supply channels to each of said delivery channels, said second layer disposed over said first surface of said first layer,
　3) a third layer having valving holes and cavities disposed over each of said at least four valving locations of said second layer, and,
　4) a pliable layer sandwiched between said second layer and said third layer, said pliable layer being flexibly responsive to suction, thereby pulling a portion of said pliable layer into an associated cavity and permitting flow through said valving location from one of said supply channel to said delivery channel, said pliable layer further being responsive to pressure to force the portion of said pliable layer against said valving location of said second layer such that flow from said supply channel to said delivery channel is prevented; and,
c) control means for communicating suction from said pneumatic means for to selected ones of said valving locations and for communicating pressure from said pneumatic means for to selected ones of said valving locations.

2. The valving system according to claim 1 wherein said control means provides pressure to each valving location not receiving suction from said pneumatic means.

3. The valving system according to claim 2 further comprising:
　a) means for selectively supplying pneumatic pressure to a selected group of said valving holes of said third layer; and,
　b) means for selectively supplying pneumatic suction to a selected group of said valving holes of said third layer.

4. The valving system according to claim 3 further comprising a first protective layer disposed between said first layer and said second layer, and a second protective layer disposed between said pliable layer and said second layer.

5. The valving system according to claim 4 wherein said second layer is composed of a chemically-reactive-resistant material.

6. The valving system according to claim 5 wherein said delivery channels and said valving locations are disposed on a side opposite said supply channels.

7. The valving system according to claim 6 further including means for flushing said delivery channels.

8. The valving system according to claim 7 wherein said means for flushing includes means for directing gaseous nitrogen into said delivery channels.

9. The valving system according to claim 8 further including:
　a) means for flushing a liquid cleanser at one end of each of said delivery channels; and,
　b) a waste reservoir selectively communicating with an opposite second end of each of said delivery channels.

10. The valving system according to claim 6 wherein said cavity of said third layer overlays a portion of said delivery channels.

11. A valve matrix comprising:
　a) a first layer having a substantially flat first surface;
　b) a second layer having at least two supply channels and at least two delivery channels, said second layer also having at least four valving locations for communicating flowing material from each of said supply channels to each of said delivery channels, said second layer disposed over said first surface of said first layer;
　c) a third layer having valving holes and cavities disposed over each of said at least four valving locations of said second layer; and,
　d) a pliable layer sandwiched between said second layer and said third layer, said pliable layer being flexibly responsive to suction, thereby pulling a portion of said pliable layer into an associated cavity and permitting flow through said valving location from one of said supply channel to said delivery channel, said pliable layer further being responsive to pressure to force the portion of said pliable layer against said valving location of said second layer such that flow from said supply channel to said delivery channel is prevented.

12. The valve matrix according to claim 11 further comprising:
　a) means for selectively supplying pneumatic pressure to a selected group of said valving holes of said third layer; and,
　b) means for selectively supplying pneumatic suction to a selected group of said valving holes of said third layer.

13. The valve matrix according to claim 12 further comprising a first protective layer disposed between said first layer and said second layer, and a second protective layer disposed between said pliable layer and said second layer.

14. The valve matrix according to claim 13 wherein said second layer is composed of a chemically-reactive-resistant material.

15. The valve matrix according to claim 14 wherein said delivery channels and said valving locations are disposed on a side opposite said supply channels.

16. The valve matrix according to claim 15 further including means for flushing said delivery channels of selected flow material.

17. The valve matrix according to claim 16 wherein said means for flushing includes means for directing gaseous nitrogen into said delivery channels.

18. The valve matrix according to claim 17 further including:
　a) means for flushing a liquid cleanser at one end of each of said delivery channels; and,
　b) a waste reservoir selectively communicating with an opposite second end of each of said delivery channels.

19. The valve matrix according to claim 15 wherein said cavity of said third layer overlays a portion of said delivery channels.

20. A peptide synthesis system comprising:
　a) a pneumatic means for providing a suction force and a pressure force;
　b) a valve block having,
　　1) a first layer having a substantially flat first surface,
　　2) a second layer having at least two supply channels and at least two delivery channels, said second layer also having at least four valving locations for communicating flowing material from each of said supply channels to each of said delivery channels, said second layer disposed over said first surface of said first layer, 3) a third layer having valving holes and cavities disposed over each of said at least four valving locations of said second layer, and, 4) a pliable layer sandwiched between said second layer and said third layer, said pliable layer being flexibly responsive to suction, thereby pulling a portion of said pliable layer into an associated cavity and permitting flow through said valving location from one of said supply channel to said delivery channel, said pliable layer further being responsive to pressure to force the portion of said pliable layer against said valving location of said second layer such that flow from said supply channel to said delivery channel is prevented;

c) at least two reaction vessels, each of said reaction vessels in communication with one of said delivery channels;

d) at least two amino acid reservoirs, each of said amino acid reservoirs in communication with one of said supply channels; and, e) control means for communicating suction from said pneumatic means for to selected ones of said valving locations and for communicating pressure from said pneumatic means for to selected ones of said valving locations.

21. The peptide synthesis system according to claim 20 wherein said control means provides pressure to each valving location not receiving suction from said pneumatic means.

22. The peptide synthesis system according to claim 21 further comprising:

a) means for selectively supplying pneumatic pressure to a selected group of said valving holes of said third layer; and, b) means for selectively supplying pneumatic suction to a selected group of said valving holes of said third layer.

23. The peptide synthesis system according to claim 22 further comprising a first protective layer disposed between said first layer and said second layer, and a second protective layer disposed between said pliable layer and said second layer.

24. The peptide synthesis system according to claim 23 wherein said second layer is composed of a chemical reactive resistant material.

25. The peptide synthesis system according to claim 24 wherein said delivery channels and said valving locations are disposed on a side opposite said supply channels.

26. The peptide synthesis system according to claim 25 further including means for flushing said delivery channels of selected flow material.

27. The peptide synthesis system according to claim 26 wherein said means for flushing includes means for directing gaseous nitrogen into said delivery channels.

28. The peptide synthesis system according to claim 27 further including:

a) means for flushing a liquid cleanser at one end of each of said delivery channels; and, b) a waste reservoir selectively communicating with an opposite second end of each of said delivery channels.

29. The peptide synthesis system according to claim 25 wherein said cavity of said third layer overlays a portion of said delivery channels.

* * * * *